(12) United States Patent
Pianka

(10) Patent No.: US 6,902,530 B1
(45) Date of Patent: Jun. 7, 2005

(54) VAGINAL SPECULUM COVER

(76) Inventor: Carla A. Pianka, 49 Candlewood Rd., Williamstown, NJ (US) 08094

(*) Notice: Subject to any disclaimer, the term of this patent is extended or adjusted under 35 U.S.C. 154(b) by 241 days.

(21) Appl. No.: 10/230,765

(22) Filed: Aug. 29, 2002

(51) Int. Cl.7 .............................................. A61B 1/303
(52) U.S. Cl. ..................................................... 600/220
(58) Field of Search ............................... 600/184, 203, 600/206, 219, 220; 128/830–841

(56) References Cited

U.S. PATENT DOCUMENTS

| | | |
|---|---|---|
| 3,841,317 A | 10/1974 | Awais |
| 5,007,409 A | 4/1991 | Pope |
| 5,072,720 A | 12/1991 | Francis et al. |
| 5,243,966 A | 9/1993 | Ng |
| 5,269,321 A * | 12/1993 | MacDonald et al. ........ 128/830 |
| 5,329,937 A | 7/1994 | Krstevich et al. |
| 5,460,165 A | 10/1995 | Mayes |
| 5,743,849 A | 4/1998 | Rice et al. |
| 5,743,852 A | 4/1998 | Johnson |
| 5,785,648 A | 7/1998 | Min |
| 6,036,638 A | 3/2000 | Nwawka |
| 6,592,514 B2 * | 7/2003 | Knight et al. .................. 600/37 |
| 2003/0069477 A1 * | 4/2003 | Ralsman et al. ............ 600/220 |

* cited by examiner

Primary Examiner—Kevin Shaver
Assistant Examiner—Michael B. Priddy
(74) Attorney, Agent, or Firm—Norman E. Lehrer

(57) ABSTRACT

A cover for a vaginal speculum that prevents the vaginal walls from collapsing and improves a physician's visibility during a surgical procedure or a gynecological examination is disclosed. The cover includes an elongated, generally tubular elastic sleeve made from a biocompatible mesh material. The sleeve has a proximal end and a distal end with an opening located at each end. The sleeve encircles and extends over the length of both of the arms of a vaginal speculum. Strings are located adjacent the proximal end of the sleeve and aid in the removal of the sleeve once the examination or procedure has been completed.

2 Claims, 2 Drawing Sheets

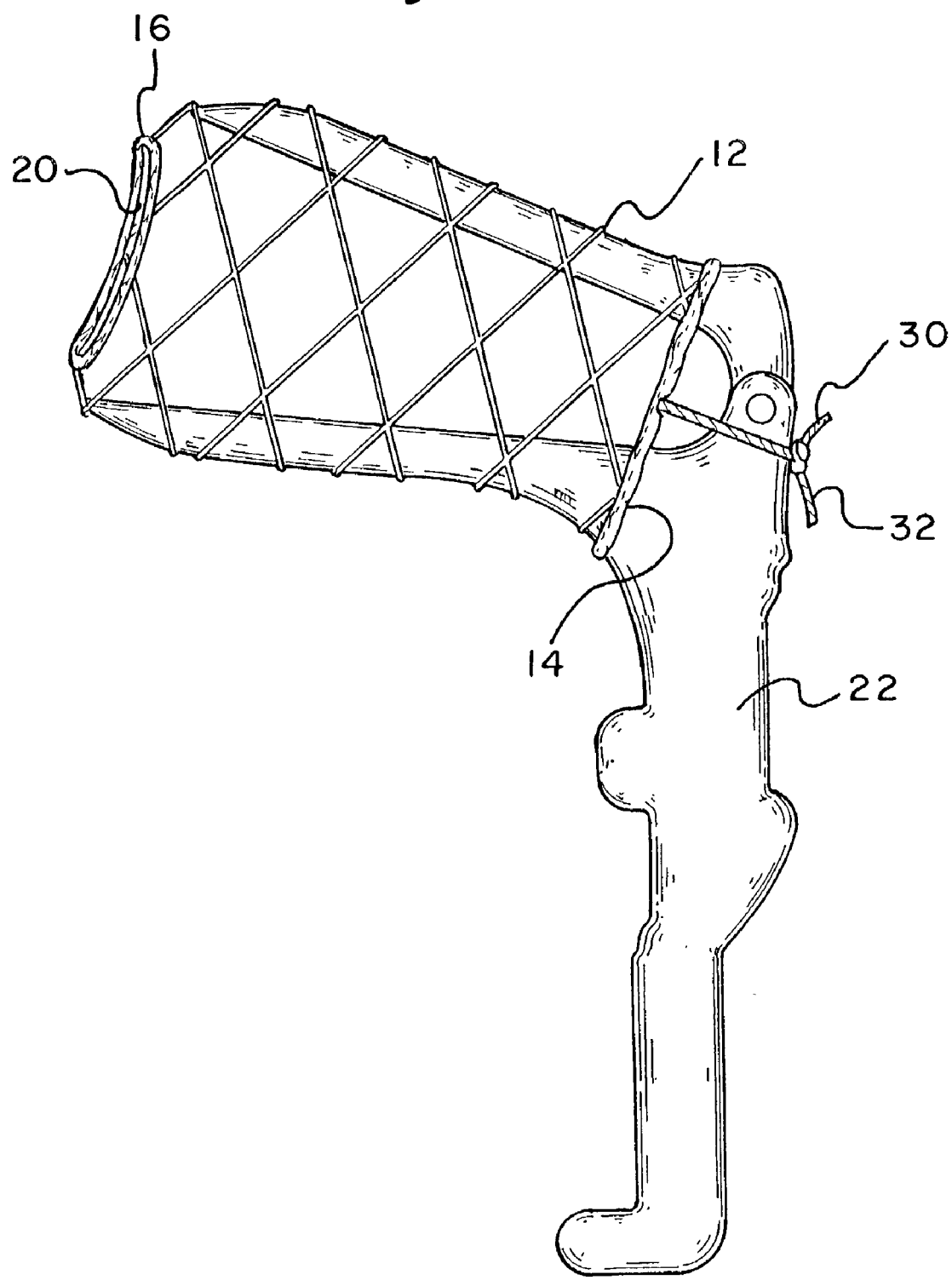

VAGINAL SPECULUM COVER

BACKGROUND OF THE INVENTION

The present invention is directed toward a cover for a vaginal speculum and more particularly, toward a cover that prevents the vaginal walls from collapsing and improves the physician's visibility during a gynecological examination or surgical procedure.

A speculum is commonly used during a gynecological examination or surgical procedure. Often, however, the vaginal walls collapse which, as a result, decreases the physician's visibility of the area being examined.

One patent that recognizes the problem discussed above and provides a solution is U.S. Pat. No. 6,036,638 to Nwawka. This patent discloses a sleeve for a vaginal speculum that appears to protect the vaginal walls and prevents them from collapsing during a gynecological examination or surgical procedure. The sleeve is made from latex and provides for a rather small hole located at the distal end of the sleeve. While the patent states that the sleeve improves the physician's visibility of the area of interest, this does not appear to be the case. First of all, latex may not be transparent, thus the physician may not be able to view the entire area. Also, the hole located at the distal end of the sleeve does not appear to allow for increased visibility by the physician. Furthermore, many patients are allergic to or react adversely to latex, thus limiting the use of this device.

Other patents disclose various types of sheaths for vaginal speculums. For example, U.S. Pat. No. 3,841,317 to Awais discloses a heat insulating shield for a speculum. This device, however, does not appear to prevent the vaginal walls from collapsing during an examination. U.S. Pat. No. 5,007,409 to Pope discloses a rubber sheath for covering each arm or blade of a vaginal speculum. The purpose of this device is reduce the pain and shock a patient experiences as a result of contacting the cold metal speculum arms or blades during an examination. Similarly, U.S. Pat. No. 5,072,720 to Francis et al. addresses the problem of patient discomfort during an examination.

Other examples of various types of shields and sheaths for vaginal speculum are disclosed in U.S. Pat. No. 5,243,966 to Ng and U.S. Pat. No. 5,460,165 to Mayes. These patents, however, appear to be concerned with preventing the spread of disease through improperly or ineffectively sterilized instruments.

Therefore, a need exists for a cover for a vaginal speculum that prevents the vaginal walls from collapsing and improves the physician's visibility during a gynecological examination or surgical procedure.

SUMMARY OF THE INVENTION

The present invention is designed to overcome the deficiencies of the prior art discussed above. It is an object of the present invention to provide a cover for a vaginal speculum that prevents the vaginal walls from collapsing during gynecological examination or surgery.

It is another object of the present invention to provide a speculum cover that improves the physician's visibility during examination or surgery.

In accordance with the illustrative embodiments demonstrating features and advantages of the present invention, there is provided a cover for a vaginal speculum. The cover includes an elongated, generally tubular sleeve made from an elastic mesh material. The sleeve has a proximal end and a distal end with an opening located at each end. The sleeve encircles and extends over the length of both of the arms of a vaginal speculum. Means for aiding in the removal of the sleeve once the examination has been completed are located adjacent the proximal end of the sleeve.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 3 is a perspective view of the cover of the present invention placed on a speculum.

DETAILED DESCRIPTION OF THE PREFERRED EMBODIMENT

Figure 1:
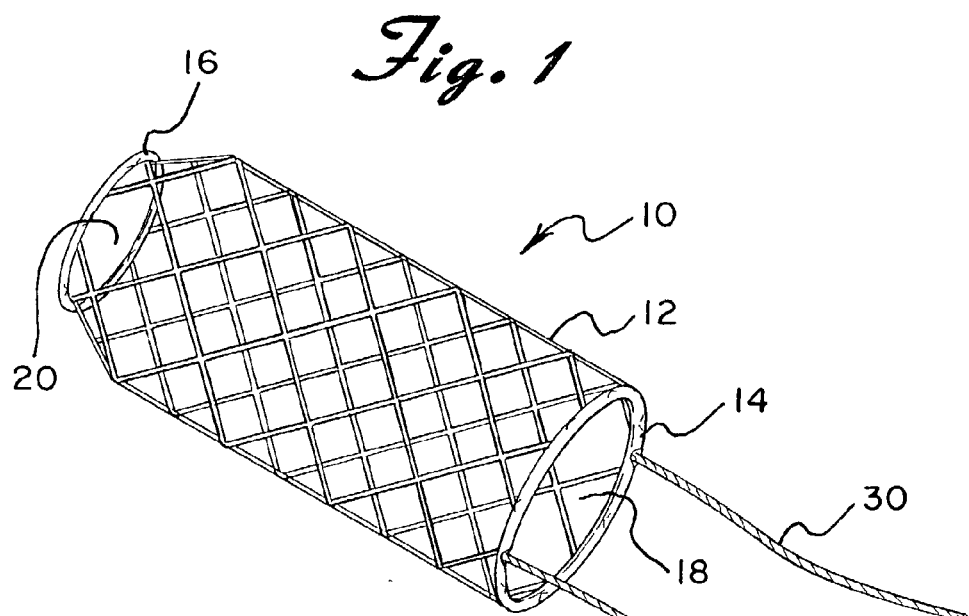
FIG. 1 is a perspective view of the cover of the present invention.

Referring now to the drawings in detail wherein like reference numerals have been used throughout the various figures to designate like elements, there is shown in FIG. 1, a cover for a vaginal speculum constructed in accordance with the principles of the present invention and designated generally as 10.

The cover essentially includes a single elongated, generally tubular sleeve 12 made from a mesh or net-like elastic material. The sleeve 12 may be made from any known biocompatible elastic material. The sleeve 12 has a proximal end 14 and a distal end 16 with an opening 18 and 20 located at each end 14 and 16, respectively. Each of the openings 18 and 20 is larger than any of the open spaces making up the mesh material. (See FIG. 1.) As can also be seen from FIG. 1, although the openings 18 and 20 are spaced apart, they are concentric and axially aligned with respect to the axis of the cover.

Figure 2:
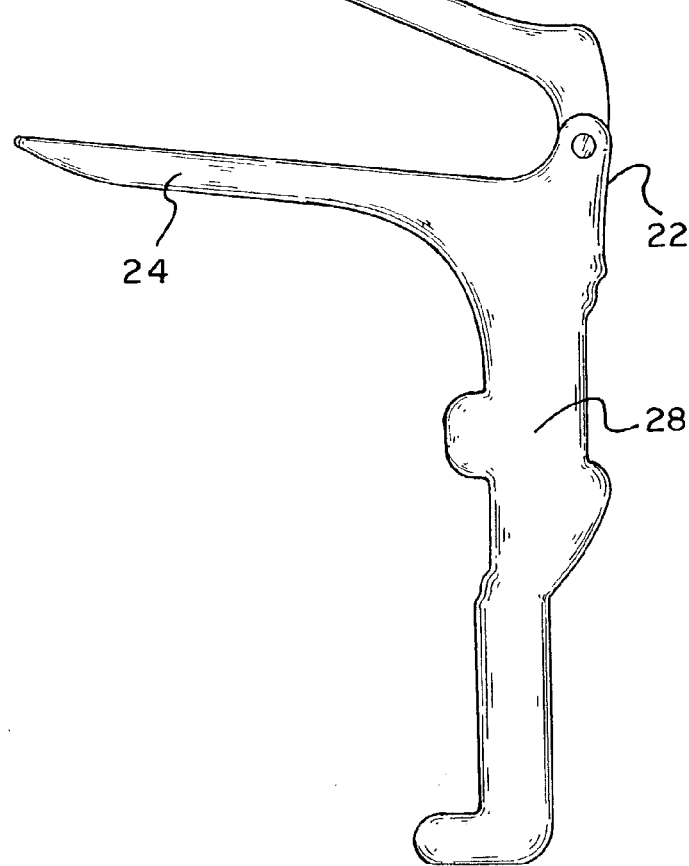
FIG. 2 is a perspective view of a conventional vaginal speculum.

A conventional vaginal speculum 22 is shown in FIG. 2. The speculum 22 typically has a lower arm 24, an upper arm 26, and a base member 28 to which the arms 24 and 26 are connected. Various mechanisms may be connected to the base member that allow the speculum arms to be opened or closed as necessary for the examination. Another example of a vaginal speculum is shown in U.S. Pat. No. 5,785,648 to Min.

In order to use the device, the sleeve 12 is placed over the closed arms 24 and 26 of the speculum 22 via proximal opening 18 so that the sleeve 12 encircles or surrounds and extends over the length of both arms 24 and 26 of the speculum 22 as well as the space between the arms 24 and 26. (See FIG. 3.) The speculum 22 may now be used in an examination or surgical procedure. The mesh material not only provides support so that the vaginal walls won't collapse, it also allows the physician to observe the entire area of interest through the openings in the mesh. The opening 20 at the distal end 16 of the sleeve 12 also allows for improved visualization by the physician.

Means 30 and 32 for aiding in the removal of the sleeve 12 once the examination has been completed are located adjacent the proximal end 16 of the sleeve 12. The aiding means may be in the form of at least two lengths of string, cord, or the like typically known and used in the art. The strings may be located at opposite sides of the proximal opening 18. (See FIG. 1.) The strings may be tied to the base member 28 of the speculum or the physician may hold, pull, or otherwise manipulate the strings while removing the speculum in order to assure that the sleeve is removed with the speculum once the examination or procedure has been completed.

The present invention may be embodied in other specific forms without departing from the spirit or essential attributes thereof and accordingly, reference should be made to the appended claims rather than to the foregoing specification as indicating the scope of the invention.

I claim:

1. A cover for a vaginal speculum used during a gynecological examination of a patient comprising:

an elongated, generally tubular sleeve made from an elastic, biocompatible mesh material, said sleeve having a proximal end and a distal end and an opening located at each of said ends, each of said openings being larger than any open spaces making up said mesh material, said openings being spaced apart but concentric, and said sleeve being adapted to encircle and extend over the length of both of arms of a vaginal speculum and means for aiding in the removal of said sleeve from the patient located adjacent said proximal end of said sleeve.

2. The cover for a vaginal speculum of claim 1 wherein said aiding means includes at least two lengths of a string located at opposite sides of said opening of said proximal end.

\* \* \* \* \*